US012433985B2

(12) United States Patent
Langenegger et al.

(10) Patent No.: US 12,433,985 B2
(45) Date of Patent: Oct. 7, 2025

(54) ASSEMBLY FOR EXTRACORPOREAL TREATMENT OF BODY FLUIDS

(71) Applicant: HEMOTUNE AG, Schlieren (CH)

(72) Inventors: Lukas Langenegger, Zürich (CH); Carlos Mora, Zürich (CH); Jean-Claude Metzger, Uitikon (CH); Ursina Haltinner, Niederlenz (CH)

(73) Assignee: HEMOTUNE AG, Schlieren (CH)

(*) Notice: Subject to any disclaimer, the term of this patent is extended or adjusted under 35 U.S.C. 154(b) by 816 days.

(21) Appl. No.: 17/764,822

(22) PCT Filed: Sep. 18, 2020

(86) PCT No.: PCT/EP2020/076145
§ 371 (c)(1),
(2) Date: Mar. 29, 2022

(87) PCT Pub. No.: WO2021/063708
PCT Pub. Date: Apr. 8, 2021

(65) Prior Publication Data

US 2022/0362450 A1 Nov. 17, 2022

(30) Foreign Application Priority Data

Sep. 30, 2019 (EP) .................................... 19200531

(51) Int. Cl.
*A61M 1/34* (2006.01)
*A61B 5/00* (2006.01)

(52) U.S. Cl.
CPC ........... *A61M 1/3486* (2014.02); *A61B 5/412* (2013.01); *A61M 2205/0277* (2013.01)

(58) Field of Classification Search
CPC .............. A61M 1/3618; A61M 1/3486; A61M 2205/0277; A61M 2205/3303;
(Continued)

(56) References Cited

U.S. PATENT DOCUMENTS 3,644,175 A 2/1972 Dasinger et al.
3,659,027 A 4/1972 Smith
5,484,396 A * 1/1996 Naficy .................... A61M 1/36 604/5.02

(Continued)

FOREIGN PATENT DOCUMENTS

EP 1 163 004 A 12/2001
EP 3 384 916 A1 10/2018

(Continued)

OTHER PUBLICATIONS

International Search Report for PCT/EP2020/076145 dated Nov. 25, 2020.
Written Opinion for PCT/EP2020/076145 dated Nov. 25, 2020.

*Primary Examiner* — Sarah Al Hashimi
*Assistant Examiner* — Meagan Ngo
(74) *Attorney, Agent, or Firm* — Sughrue Mion, PLLC

(57) ABSTRACT

A method for extracorporeal treatment of a body fluid of a patient suffering from sepsis, in an extracorporeal flow line, comprising removing at least one harmful substance from the body fluid of the patient. In a first injection step, a first mixture containing functionalized magnetic particles bound to at least a first binding agent at least directed against a first type of target molecules contained in the body fluid is added to the extracorporeal flow line comprising a sample of the body fluid extracted from a patient and containing at least the first type of target molecules. The first mixture is injected in a therapeutically effective dose necessary to reduce a concentration of the target molecules of at least the first type in the body fluid sample of the patient, followed by a mixing step and a separation step for reduction of the target molecule concentration.

24 Claims, 2 Drawing Sheets

(58) Field of Classification Search
CPC .. A61M 1/3475; A61M 1/3679; A61M 1/342; A61M 1/3621; A61M 1/0236; A61M 1/36; A61M 1/361; A61B 5/412
See application file for complete search history.

(56) References Cited

U.S. PATENT DOCUMENTS

| | | | | |
|---|---|---|---|---|
| 5,853,722 | A | 12/1998 | Rollins et al. | |
| 6,616,623 | B1 * | 9/2003 | Kutushov | A61M 1/36 210/695 |
| 2002/0058030 | A1 * | 5/2002 | Monroy | A61M 1/3618 424/140.1 |
| 2002/0147094 | A1 * | 10/2002 | Dolecek | B04B 9/10 494/9 |
| 2002/0187069 | A1 * | 12/2002 | Levin | A61M 1/34 422/44 |
| 2009/0136586 | A1 | 5/2009 | Larm et al. | |
| 2009/0192434 | A1 | 7/2009 | Thorn et al. | |
| 2011/0224645 | A1 * | 9/2011 | Winqvist | B01J 20/3242 530/324 |
| 2013/0102948 | A1 * | 4/2013 | Reich | A61M 1/3621 210/641 |
| 2013/0178834 | A1 * | 7/2013 | Greenberg | A61M 1/3606 435/5 |
| 2014/0008210 | A1 * | 1/2014 | Guia | G01N 33/491 204/518 |
| 2019/0240663 | A1 | 8/2019 | Miller et al. | |
| 2021/0220533 | A1 * | 7/2021 | Liberti | A61M 1/3618 |

FOREIGN PATENT DOCUMENTS

| | | | |
|---|---|---|---|
| WO | 00/08463 | A2 | 2/2000 |
| WO | 00/58005 | A2 | 10/2000 |
| WO | 2012/135834 | A2 | 10/2012 |

* cited by examiner

ASSEMBLY FOR EXTRACORPOREAL TREATMENT OF BODY FLUIDS

CROSS REFERENCE TO RELATED APPLICATIONS

This application is a National Stage of International Application No. PCT/EP2020/076145 filed Sep. 18, 2020, claiming priority based on European Patent Application No. 19 200 531.2 filed Sep. 30, 2019.

TECHNICAL FIELD

The present invention relates to an ex vivo method for extracorporeal treatment of a body fluid of a patient suffering from a dysregulated immune response, especially from sepsis, comprising removing at least one harmful substance from a body fluid sample of the patient.

PRIOR ART

Sepsis, a serious infection-related multiple organ dysfunction, has been the most frequent cause of death in hospitalized patients in the 21$^{st}$ century. Sepsis is a multi-step process that involves an uncontrolled inflammatory response by host cells that may result in multi-organ failure and death. Unlike other major epidemic illnesses, treatment for sepsis so far has been nonspecific, and limited primarily to support of organ function and administration of intravenous fluids, antibiotics, and oxygen. There are no approved drugs that specifically target sepsis. Immense expenses are incurred due to long stays of septic patients in intensive care units. In 2017, the WHO declared sepsis a global health priority by adopting a resolution to improve the prevention, diagnosis and management of sepsis. Thus, there is a great need for an effective therapeutic approach against this disease. The key factor of immune resolution is the balance between pro-inflammatory and anti-inflammatory forces. Although both pro-inflammatory and anti-inflammatory processes begin promptly after sepsis initiation, at the beginning there is usually a predominance of an initial hyper-inflammatory phase, the scale of which is determined by many factors including pathogen virulence, bacterial load, host genetic factors, age, and host comorbidities, followed by an anti-inflammatory process. In the later phase, in septic patients and in patients with severe non-infectious SIRS (Systemic Inflammatory Response Syndrome, such as burns, trauma, major surgery, haemorrhage, or ischemia-reperfusion after cardiac arrest), the anti-inflammatory process may overwhelm the pro-inflammatory forces. Today, it is well established that many critically ill patients either show signs of co-existing inflammatory and counter-regulatory anti-inflammatory response early in critical illness or will undergo transition from early pro- to later anti-inflammatory phenotypes. The "net effect", i.e., the resulting phenotype, of such profound anti-inflammation is referred to as "sepsis-(or injury-) associated immunosuppression (SAIIAI)". It is estimated that over half the patients with sepsis develop immunosuppression. It has been recognized that not the initial hyper-inflammatory state, but rather a profoundly suppressed state of the immune system accounts for the majority of sepsis-related deaths. Sepsis-induced immunoanalysis comprises an ineffective clearance of septic foci, and renders the septic patient more vulnerable to secondary infections, as well as reactivation of latent infections and therefor results in increased mortality.

Immunosuppression is characterized by impaired innate and adaptive immune responses including monocytic deactivation with diminished HLA class II surface expression, diminished release of pro-inflammatory mediators, and reduced phagocytosis, resulting in impaired clearance of infection. This may be associated with enhanced immunological tolerance, increased immune cell apoptosis, and altered gene expression profiles. Interestingly, recent data show that respective changes are not exclusive to circulating immune cells and that comparable anti-inflammatory phenotypes can be found, e.g., in splenic or lung tissue and other solid organs. Immune-stimulatory treatment has thus been emerging as a possible adjunctive treatment for sepsis.

Septic shock is a potentially fatal medical condition that occurs when sepsis, which is organ injury or damage in response to infection, leads to dangerously low blood pressure and abnormalities in cellular metabolism. Both pro-inflammatory and anti-inflammatory responses play a role in septic shock, which involves a widespread inflammatory response that produces a hypermetabolic effect.

Many types of microbes can cause sepsis, including bacteria, fungi, and viruses. However, bacteria are the most common cause. Both gram-negative and gram-positive bacteria play a major role in causing sepsis. These bacteria produce a range of virulence factors that enable them to escape the immune defenses and disseminate to remote organs, and toxins that interact with host cells via specific receptors on the cell surface and trigger a dysregulated immune response. More than half of all cases of septic shock are caused by gram-negative bacteria. Endotoxins are bacterial membrane lipopolysaccharides (LPS) produced by gram-negative bacteria, and cause an immune response. The effects of these toxins are mediated primarily by tumor necrosis factor alpha (TNF$\alpha$) and other cytokines, including IL-1 (Interleukin 1), IL-6 and IL-8, being massively released by monocytes, macrophages and other leukocytes. These cytokines in turn have profound effects on other cells of the immune system as well as on other types of cells. Parallel to the stimulation of monocytes and macrophages, the complement system is activated, wherein the C3 and C5 proteins and their cleavage products C3a and C5a play a central role.

Due to a lack of available treatments, standard of care of sepsis patients is limited to infection control and supportive care.

Methods directed against removal of unwanted pro-inflammatory components from patient's blood have been developed. Methods for removing endotoxin impurities from the blood, e.g. for the manufacture of blood products, include sterilization, irradiation with $\gamma$-rays, treatments with acids or bases, as disclosed e.g. in U.S. Pat. No. 3,644,175 or U.S. Pat. No. 3,659,027. Further procedures include expensive plasma exchange therapy in which the patient's plasma is replaced partially with a plasma substitute free of the harmful component(s). However, potentially beneficial components are also removed from the patient, and there is a high risk of transferring infections.

Other procedures use membranes to filtrate the blood, but these methods lack selectivity and concurrently also remove proteins that then need to be replaced again. Hemoperfusion or hemopurification is an extracorporeal medical process used to remove toxic or unwanted substances from a patient's blood. Typically, for this purpose, blood is passed over an adsorbant substance. Various methods of treating sepsis by extracorporeal adsorption to unspecifically binding substances, such as activated carbon, ion exchange resins, etc. have been described.

Known treatments of body fluids include the unspecific adsorption of a broad range of inflammatory molecules, as e.g. described in EP 3384916. WO 00/58005, WO 00/08463 EP 1163004, and U.S. Pat. No. 5,853,722 disclose therapies involving immune-adsorption with polymeric carriers comprising antibodies directed against endotoxins and/or complement factors, and/or TNF and/or interleukins, while US 2009/0136586 uses carbohydrates bound to a solid substrate and having an affinity for various targets.

Later, immune status characterization in larger patient cohorts using novel biomarkers allowed for a more profound understanding. When looking at an individuals' immune response, a high inter-individual variance and highly dynamic changes can be observed over time.

So far, no pharmacologic agents have been demonstrated to improve the outcome of Systemic Inflammatory Response Syndrome (SIRS). Only one drug has been approved for treating severe sepsis in adults: recombinant human activated protein C (rhAPC), or Drotrecogin alfa (activated). However, this drug was withdrawn because it was targeted at the pro-inflammatory state of SIRS as the cause of sepsis with dismal results.

In the past decade, the sepsis research field has shifted focus from targeting the early hyperinflammation to reversing persistent sepsis-induced immunosuppression. It has been recognised that effective correction should blunt hyperactive responses or boost suppressed responses.

Different combinations of host and pathogen characteristics and interactions among them may lead to the same clinical picture. Therefore, universally applicable diagnostic criteria and treatment algorithms are difficult to be defined. In other words, while sepsis is a dysregulated immune response to infection comprising heterogenous patient populations which vary in etiology and severity, treatment methods of the state of the art do not take into account the actual elimination capacity of an individual's immune system and therefore do not address the specific immunological status of an individual patient. The same drug or treatment may be beneficial, non-effective or even harmful depending on the patient's immunological status. It is the host's immune response that determines the severity and outcome of sepsis. Patients with critical illness respond differently to injury or pathogenic insult. Whereas patient "A" may undergo a pronounced inflammatory phase with regain of immunological homeostasis and subsequent survival, patient "B" may enter a persisting phase of injury-associated immunosuppression (IAI), in which viral reactivation rates, secondary (re-) infection rates, and mortality is increased. This underlines the importance of inter-individual response patterns and need for individual patient characterization before application of interventional therapeutic approaches (Pfortmueller et al., "Assessment of Immune Organ Dysfunction in Critical Illness: Utility of Innate Immune Response Markers". Intensive Care Medicine Experimental 5, no. 1 (Oct. 23, 2017): 49).

The dysregulated immune response characterized by sepsis involves multiple pathways and mediators. So far, single-agent therapeutic interventions to block particular pathways or processes have failed.

Furthermore, sepsis is an acute condition. During the course of sepsis, patients go through different phases in which different biological mechanisms drive disease progression. Mediators which might be dominant in one phase are probably much less important in another. For example, IL-1 or TNFα are predominantly present in the hyper-inflammation phase and have a short circulation time. Once patients have gone through the hyper-inflammation phase, their plasma levels decrease and targeting of these molecules will most likely not lead to any patient improvement. If disease related compounds are not targeted at the stage when they are driving sepsis progression, intervention targeting these compounds will most likely have no effect. The clinician has to rely on the etiology, clinical picture and biomarkers in order to detect the onset of a potentially devastating new infection as soon as possible. The heterogenous disease stage of patients at intensive care unit admittance, fast disease progression of sepsis and lack of thorough patient characterization made intervention timing very difficult, leading to inconclusive sepsis trials.

SUMMARY OF THE INVENTION

It therefore is an object of the present invention to provide an individual approach for treatment, i.e. a more personalized immune therapy that considers an individual's immune functionality, in order to improve the outcome of the therapy in treated patients. In other words, the present invention focuses on separately and selectively targeting the inflammatory mediators according to a specific patient's current immunological status. The present method focuses mainly on sepsis patients, on the one hand, with hyperinflammation, and especially those with sepsis-induced immunosuppression, as immunosuppressed patients show prolonged length of stay in the intensive care unit and are at high risk of death or secondary infection (deaths of patients with sepsis-induced immunosuppression account for 65% of total sepsis mortality). The goal underlying the present invention is to restore immune function by action on multiple key pathways, thereby improving clinical outcomes for patients suffering from persistent sepsis-induced immunosuppression.

For this purpose, a sample of body fluid, preferably blood, is provided, or taken from a patient's circulation and treated before it is returned to the circulation. The therapeutic assembly to perform the described immunoadsorption comprises an extracorporeal flow line, which is defined here as the entire apparatus carrying the blood outside of the body. For this purpose, the extracorporeal flow line comprises two connection ports to the patient, wherein a first connection port comprises the inlet of untreated body fluid from the patient or the inlet of the sample of untreated body fluid of the patient into the flow line. A second connection port comprises the outlet of treated body fluid to the patient from the flow line (veno-venous or veno-arterial). Between the two connection ports, an extracorporeal flow line carries the blood outside of the body, possibly driven by a fluid pump to pump the blood through the extracorporeal flow line.

The present invention concerns a method for extracorporeal treatment of a body fluid of a patient suffering from a dysregulated immune response, especially from sepsis, in an extracorporeal flow line. In most cases, the dysregulated immune response is caused or aggravated by an insult by a pathogenic microbe, an inflammatory cell or an inflammatory protein. Such a dysregulated immune response can also be the result of an autoimmune disease. The method comprises removing at least one harmful substance from a sample of the body fluid of the septic patient, comprising the following steps:

A first injection step, in which, by means of a first injection device, a first mixture containing functionalized magnetic particles bound to at least a first binding agent at least directed against, i.e. having a binding affinity for, a first type of target molecules contained in the body fluid, preferably blood, is added to an extracorporeal flow line comprising a sample of the body fluid extracted from a patient suffering from a dysregulated immune response, especially from sepsis, said body fluid containing at least target molecules of the first type. The first mixture containing the at least first binding agent is added in a therapeutically effective dose, i.e. comprising the binding agent at a concentration and dose necessary to reduce a concentration of the target molecules of at least the first type in the sample of body fluid of the patient.

Subsequently, the body fluid now comprising the functionalized magnetic particles of the first mixture is mixed, in order to ensure sufficient binding of the target molecules of at least the first type to the functionalized magnetic particles.

Subsequently, the functionalized magnetic particles bound to the target molecules of at least the first type are separated from the sample of body fluid of the patient, such that a concentration of target molecules of at least the first type in the sample of body fluid is reduced. For security purposes, also excessive functionalized magnetic particles not bound to target molecules are also filtered out.

The first injection step is controlled based on data obtained, i.e. collected from the sample of the patient's body fluid, said data providing information about the immunological status of the patient. Based on said data, the first injection step is controlled in terms of at least one of the following: injection rate, time of injection, injection dose, concentration, injection pressure. The data is obtained by submitting a portion of the body fluid sample to an assay or directly measuring parameters in the body fluid within the flow line by means of at least one sensor as further described below.

Preferably, the method according to the present invention comprises at least a second injection step, in which, preferably by means of a second injection device, a second mixture, different from the first mixture, containing functionalized magnetic particles is added to the extracorporeal flow line comprising the body fluid extracted from the patient suffering from sepsis. The second injection step is carried out upstream of, downstream of or simultaneously with the first injection step. The first injection step and the second injection step are each individually controlled separate from each other based on data providing information about the immunological status of the patient. The injection parameters of the second mixture containing the second binding agent, such as injection rate, time, amount, concentration, etc. can be controlled separately, but in coordination with the injection of the first mixture.

In the second injection step, the functionalized magnetic particles contained in the second mixture are preferably bound to at least a second binding agent different from the at least first binding agent and at least directed against a second type of target molecules contained in the body fluid and different from the first type of target molecules.

As an alternative, in the second injection step, the second mixture, instead of or in addition to a second binding agent, contains the at least first binding agent, however at a different concentration than in the first mixture.

The first and/or second mixture preferably is a slurry, suspension or dry powder, contained in buffer or other reagents. Preferably the first and/or the second mixture has an effective therapeutic concentration of selected binding agents necessary to reduce the concentration of the corresponding target molecules. The concentration of the corresponding target molecule(s) is preferably reduced to a predetermined value, e.g. according to standard-values or calculated by a processor in a control unit based on data received by a diagnostic unit.

The inventive method can further comprise at least a third or further injection step comprising a third or further injection mixture, wherein the third injection step is individually controlled separately from the first injection step and/or the second injection step.

Preferably, the method further comprises, upstream of the first injection step and/or the second or any further injection step, a diagnostic step, in which said data providing information about the immunological status of the patient is obtained. Therein, preferably an expression or concentration of at least one target molecule or marker molecule, respectively, in the body fluid of the patient is measured in an assay or by a sensor. Preferred assays include an endotoxin activity assay (EAA) or an enzyme-linked immunosorbent assay (ELISA).

The diagnostic step serves to, first of all, define or detect and identify an excessive or insufficient concentration of at least one type of immune status biomarker molecule in the body fluid. "Excessive" or "insufficient" in this context means a pathophysiological or abnormally high or -low concentration or level of expression, when compared to a predetermined value provided by a standard, a computer program, or data entered by a physician.

Before undergoing the proposed extracorporeal treatment, the patients preferably previously undergo a clinical assessment. Based on the results of the clinical symptoms, in combination with the age of the patient and possible comorbidities, a "high-risk" patient subgroup can be defined. For this subgroup, preferably, in addition to the clinical assessment, the body fluid is submitted to a further immunological characterization. Especially in case an immune suppression is suspected based on the results of the clinical symptoms, a physician can decide to additionally carry out the more costly immunological phenotyping by using immune status biomarkers that reflect both innate and adaptive immune function. An example for such an immune status biomarker is monocytic human leukocyte antigen-DR (mHLA-DR). Diminished mHLA-DR on circulating monocytes is a reliable marker for the development of immunosuppression in critically ill patients. Indeed, decreased expression of this marker is regularly reported to be associated with higher mortality or risk for nosocomial infections in critically ill patients.

Immunoanalytical/immunosuppression mechanisms are multifold. Detection of a reduced mHLA-DR expression by flow cytometry or immunohistochemistry, or detection of reduced TNFα production upon ex vivo stimulation and cytokine determination by ELISA or comparable method, are indicators or markers for monocyte deactivation.

An increased expression of one of the negative regulatory molecules PD-(L) 1 or CTLA-4 and BTLA, or of LAG-3 and TIM-3 can be detected by flow cytometry or immunohistochemistry. A decreased expression of the IL-7 receptor is detected by flow cytometry or immunohistochemistry is an indicator for downregulation of receptors.

An increased expression of sFAS or FAS-L can be detected by ELISA and is an indicator for apoptosis. This is also true for a reduced expression of the number of (specific subsets of) lymphocytes, which can be detected by assessing leukocyte differention and flow cytometry. The total lymphocyte count can also serve as a more simple marker to detect immunosuppression. A suppression of immune cells can be suspected if the expression of CD4+ and CD25+ (Treg) cells or of myeloid-derived suppressor cells (MDSC) is shown to be increased by flow cytometry. An increased concentration of anti-inflammatory cytokines such as IL-10, IL-13, IL-4, IL-1ra, TGF-β, or an increase in the ratio of IL-10/TNF-α can be assayed by ELISA or a comparable method.

Preferably, besides the assaying of general markers, also genomics or metabolomics are used to achieve a more detailed characterization of the immune status.

Provided that a pathophysiologic change is detected in the blood, e.g. indicated by an above- or below normal concentration or expression of an immune status biomarker molecule that is associated with sepsis, the data received from the immunological assessment is used to adapt the therapeutic treatment in an individual and time-dependent manner, by extracting specific target molecules, whose excessive concentration results in the pathophysiological expression pattern of the biomarkers mentioned above.

The assessment or diagnosis in the diagnostic step of the extracorporeal treatment may either take place by taking a sample of the body fluid, preferably blood, from the patient and running an assay or by measuring a concentration of a specific target molecule in an aliquot of the sample or directly in the flow line by means of at least one sensor.

For carrying out the diagnostic step, the assembly thus comprises, in a further preferred embodiment, preferably upstream of the first and/or any further injection device, a diagnostic unit. The extracorporeal flow line may thus comprise or be connected to or associated with a diagnostic unit, such that the untreated body fluid, after entering the extracorporeal flow line, undergoes a diagnostic test based on which e.g. type, concentration and amount of the substance to be injected is chosen. Therein, additional data providing information about the immunological status of the patient is obtained. For this purpose, the extracorporeal flow line may contain a diagnostic sample port, via which a test sample or aliquot of the body fluid can be extracted, to be transferred to an external or associated diagnostic device for testing/analysis. The use of such a sample port enables the monitoring of a patient's immunological status over the duration of the treatment.

"Untreated" in the sense of this application is to be understood as "untreated" in terms of the specific sample of body fluid presently contained in the extracorporeal flow line or in the current pass/round of treatment. It can include body fluid previously treated in previous passes/rounds of treatment in the same or other extracorporeal flow lines. Perhaps a sample of body fluid is guided through the flow line for a first round of treatment by injecting a first injection mixture, followed by a first separation step, and then enters the flow line again for at least a second round of treatment at a later stage, in which at least a second injection mixture is injected, followed by at least a second separation step.

If the extracorporeal flow line is connected to the patient's body, it is possible to continuously extract body fluid from the patient's body, diagnose it, treat it in the extracorporeal flow line, possibly diagnose it again, and return treated body fluid to the patient's body continuously. Such an extracorporeal circuit enables a continuous treatment of the body fluid, such as blood. By repeating the diagnostic step, and, if necessary, also including immune status phenotyping, various times during treatment, and adapting the treatment according to the dynamic changes in the immunological status of the patient, it is possible to optimally respond to the patient's need over time. Should for example the patient be administered drugs, such as antibiotics as a treatment of an infection, which may trigger an undesired response in the patient's body during the course of the treatment, such as the release of certain immune activators or suppressors in the body, this can be taken into account and the treatment in the extracorporeal flow line can be adjusted such as to extract an excess amount of these undesired substances from the body fluid.

In the diagnostic unit, after determination of an excessive or insufficient concentration of a biomarker molecule associated with the pathological immune status, an excessive concentration of at least a first and/or a second or any further type of target molecule in the body fluid is identified, and a suitable or necessary type and concentration of a corresponding at least first and/or second or further binding agent is selected. The selected binding agent(s) is/are capable of binding to the at least first and/or second or further identified target molecule(s) to be bound to the magnetic particles to be injected by at least the first and/or second or further injection device. Thereby, the concentration of the respective target molecule(s) can be lowered to a desired value by removal from the body fluid sample.

The diagnostic step according to one preferred embodiment is carried out in that upstream of the at least first injection step, a concentration of a first type of target molecules in the body fluid is measured, preferably by a first sensor. Preferably, upstream of the at least second injection step, a concentration of at least the second type of target molecule in the body fluid is measured separately, either by the same, first sensor or by a different, second sensor. Alternatively, a sample of body fluid can be extracted from the extracorporeal flow line at different points along the extracorporeal flow line, and analysed in the above mentioned diagnostic unit, e.g. by an assay. The data, e.g. concentration data, resulting from the diagnostic step, i.e. from the diagnostic unit, e.g. the corresponding sensor or assay, serves as a basis for selecting the appropriate type of the at least first and/or second or further binding agent which is capable of binding to the identified at least first and/or second or further type of target molecule to be bound to the magnetic particles which are injected in the first and/or second or further injection step. Then, an effective therapeutic concentration of the respective binding agent(s) bound to functionalized magnetic particles to be added to the body fluid is calculated based on the data received.

The diagnostic step and its analysis, and therefore also the selection of the type and concentration of the binding agent necessary or suitable for injection is carried out either by a diagnostic device or by a physician. Data obtained in the diagnostic step from the patient's body fluid providing information about the immunological status of the patient is then preferably transmitted to a control unit which is arranged in an electrical or wireless communication with the extracorporeal flow line. The control unit preferably controls at least the first injection step. Preferably, the control unit comprises a user interface. The control unit: provides information to a user or physician, allowing to determine or select at least one of the following: the type of target molecule, type of binding agent, type of nanosorbent, concentration of mixture to be injected, dose, pressure, time of injection, length of treatment, number of cycles (if continuous), etc.

Preferably, the concentration of one or more target molecules of interest in the blood is monitored at the beginning and at the end of the extracorporeal flow line to determine the concentration of endotoxins and other removed targets to show a "single pass removal". Preferably, endotoxins, as well as IL-10, one of the main anti-inflammatory cytokines, and e.g. C5a, one of the most potent inflammatory peptides of the complement system, and e.g. IL-6, an important cytokine with both pro- and anti-inflammatory functions and correlating closely with clinical severity in inflammatory disease and fatal outcome in patients with sepsis, are measured, preferably immediately before and after each cycle of treatment. For this purpose, a second or further diagnostic unit or diagnostic sample port can be arranged downstream of the separation unit or separation step, respectively.

It is especially advantageous, if the diagnostic patient data is stored for subsequent analysis, e.g. on a computer or a separate storage unit. The results of the analysis can then serve for the development and improvement of treatment algorithms, and for defining patient populations and finally possibly also for developing optimal pharmaceutical products for specific patient populations.

The functionalized magnetic particles injected in the first injection step and/or any further injection steps, preferably are nano-size magnetic adsorbents, so-called nanosorbents.

Each of the magnetic particles preferably comprises a magnetic core and at least one functional layer, wherein preferably the functional layer comprises at least a first sub-layer comprising an antifouling substance to prevent non-specific absorption and a second sub-layer comprising an affinity binding structure for binding the respective target molecule of at least the first type and/or the second type.

According to a preferred embodiment, in the first injection step and/or in the second injection step, the first binding agent and/or the second binding agent, or any further binding agent, bound to the functionalized magnetic particles is selected from the following group: antibodies, peptides, lectines, chemical chelating agents, polymers, wherein preferably, the at least first binding agent and/or the at least second binding agent is an antibody or an aptamer, at least directed against or having a binding affinity for the first type of target molecule and/or the second type of target molecule. In case of an antibody, the at least first binding agent in the first mixture, and/or the at least second binding agent in the second mixture can be either a monoclonal or a polyclonal antibody.

In case of an aptamer, this short, single stranded nucleic acid sequence can either be an DNA- or a RNA-oligonucleotide.

The at least first binding agent, which is bound to the functionalized magnetic particles, is preferably directed at least against a first type of target molecule or marker selected from the group of: pathogen-associated-molecular-pattern immune activators, pro-inflammatory mediators, anti-inflammatory mediators, complement factors, or cleavage products thereof, wherein preferably, the first binding agent, is directed at least against a first type of target molecule selected from the following group and/or the second binding agent is directed at least against a second type of target molecule selected from the following group: cytokines, nitric oxide, thromboxanes, leukotrienes, phospholipids (like platelet-activating factor), prostaglandins, kinins, complement factors such as e.g. C5, C3, or their cleavage products, e.g. C5a, C3a, coagulation factors, superantigens, monokines, chemokines, interferons, free radicals, proteases, arachidonic acid metabolites, prostacyclins, beta endorphins, myocardial depressant factors, anandamide, 2-arachidonoylglycerol, tetrahydrobiopterin, cell fragments and chemicals including histamine, bradykinin, and serotonin. More preferably, the at least first binding agent is directed at least against a first type of target molecule selected from the following group and/or the at least second binding agent is directed at least against a second type of target molecule selected from the following group: LPS, lipotechoic acid, TNFα, IL-1, IL-6, IL-8, IL-10, IL-15, IL-18, IL-33, HMGB1 (High-Mobility-Group-Protein B1), GM-CSF, IFNγ, C5a, C3a, serine proteases, e.g. C5-convertase or C3-convertase, serine peptidases, e.g. C5a peptidase, or C3a peptidase, peptide hormones, such as e.g. adrenomedullin (ADM).

In case of a second or further injection step with a second or further injection mixture, any second and/or further type of target molecule to be bound to any second or further binding agent of a further type in the method of the present invention is preferably also selected from the above mentioned groups.

The term “target molecules”, for the purpose of this application, can be understood, in the broader sense, as target compounds, including molecules as well as larger proteins of high molecular weight, and assemblies or aggregates of molecules, such as e.g. micelles of LPS. Also pathogens as such, i.e. bacterial-, viral-, fungal cells, or immune cells, such as neutrophils, monocytes and regulatory T-cells (TReg) can serve as target compounds or target molecules to be extracted from the body fluid, e.g. from blood.

According to a further preferred embodiment, any of the injection steps mentioned can also comprise the injection of a dose of a medicament for the treatment of the patient. Said dose of a medicament can be contained in a pre-mixed injection mixture, or can be injected from a separate container prior to, together with or subsequently to the injection of the functionalized magnetic particles. The dosing parameters, i.e. time and rate of injection, choice and concentration of the medicament, is preferably controlled by the controller, especially by an algorithm based on an analysis of the diagnostic data.

The present invention further concerns an assembly for extracorporeal magnetic separation-based body fluid purification of a patient suffering from a dysregulated immune response, e.g. from sepsis, comprising an extracorporeal flow line. Therein, the assembly comprises an extracorporeal flow line interconnected between an inlet port and an outlet port for attachment to the patient’s body. The inlet port serves for the entry of untreated blood into the extracorporeal flow line from the patient’s circulation, or for the injection of a sample of untreated blood into the extracorporeal flow line. Equally, the outlet port of the flow line serves for returning the treated blood exiting from the extracorporeal flow line into the patient’s circulation, in case of an extracorporeal circuit, or for extracting the sample of treated blood after the respective cycle from the extracorporeal flow line, e.g. for storage for later use, for further treatment, analysis, or for injection into the untreated patient, in case of a non-continuous treatment method.

The assembly further comprises at least a first injection device for injecting a first mixture comprising functionalized magnetic particles bound to at least a first binding agent at least directed against a first type of target molecule contained in the body fluid into the extracorporeal flow line.

The assembly preferably further comprises a mixing unit, for mixing the functionalized magnetic particles in the body fluid after injection of the functionalized magnetic particles to allow a therapeutically effective level of complexation or binding between the functionalized magnetic particles and the first type of target molecule.

The mixing step can for example take place in a separate mixing unit downstream of the first and/or second injection device. In one embodiment, the magnetic particles and the body fluid enter the mixing unit through one common tube, in which case at least one injection device is located upstream of the mixing unit. In one embodiment, the body fluid enters an injection device comprising a mixing chamber and at least one injection device, wherein the mixing chamber comprises one inlet for the body fluid and a separate inlet for at least one injection device or for the contents of such an injection device. The body fluid in this case contacts the functionalized magnetic particles in said mixing chamber.

It can be advantageous if after every injection step, an individual mixing step is carried out, in which case, at least one mixing unit is arranged along the extracorporeal flow line downstream of or in the at least one injection device. Thus, a first mixing unit can be located downstream of or in a first injection device and a second mixing unit downstream of or in a second injection device. Alternatively, the assembly can comprise one or more mixing units, each comprising several individual separate inlets: a first inlet for the body fluid, and at least one additional inlet for the functionalized magnetic particles from an injection device connected to the mixing chamber. In one embodiment, the first and the second injection devices therefore each inject the functionalized magnetic particles into the mixing unit, which also receives, through a separate inlet, the body fluid to be treated. In a different embodiment, a first injection device injects magnetic particles into a first mixing chamber which receives the untreated body fluid, and a second injection device injects magnetic particles into a second mixing chamber downstream of the first mixing chamber, which separately receives the body fluid. In these cases, where the body fluid and the magnetic particles enter the mixing chamber(s) separately through different inlets or tubes, the magnetic particles contact the body fluid for the first time in the mixing unit and not upstream thereof. Alternatively, the mixing step can also be carried out along the flow line, e.g. by providing a vortical flow to the flow line. The mixing unit furthest downstream in the flow line is then in fluid communication with the magnetic separation unit which is located downstream of the mixing unit.

Preferably, the functionalized magnetic particles are mixed with the body fluid sample prior to entering the magnetic separation unit.

The mixing unit can also be a portion of the extracorporeal flow line itself, which can be, but not necessarily, formed, e.g. wound or deflected in a specific manner to impose a vertical flow to the contents of the flow line to ensure enough exposure time of the functionalized magnetic particles to the target molecules in the body fluid before the body fluid continues along the flow line to a magnetic separation unit.

The assembly according to the present invention further comprises a separation unit for carrying out a separation step, comprising a magnetic field region for magnetically separating the functionalized magnetic particles and the target molecules bound thereto from the body fluid. Preferably, the magnetic separation unit comprises at least one magnetic filter, preferably a permanent magnetic filter. As an alternative, the magnetic filter could be controlled by a control unit associated with the extracorporeal flow line. Preferably, it contains an external magnet, a filter formed from a magnetically attractive material and a container. The magnet preferably is a permanent magnet, in order to ensure that no magnetic particles remain in the treated sample and thus to prevent any magnetic particles from entering the patient's body, however, alternatively an electromagnet can also be used. The container preferably comprises an inlet and an outlet. The mixture of body fluid and magnetic particles enters the magnetic separation unit through the inlet and the treated sample exits in form of a filtrate through the outlet and is collected for storage or return of the treated sample to the patient's body. In order to prevent magnetic particles from entering the patient's circulatory system, according to another preferred embodiment, the assembly comprises, downstream of the magnetic separation unit, a sensor for determining the presence of remaining magnetic particles in the body fluid. In case magnetic particles remain in the flow line after the magnetic separation, the control unit will direct the flow of the body fluid either again through the magnetic separation unit it came from or through a further magnetic separation unit for an additional separation step. If the body fluid is determined to be free of magnetic particles, the flow of the body fluid is directed to the outlet of the extracorporeal flow line, where it is collected for storage or transport or immediately returned to the patient.

The assembly preferably further comprises at least one control unit which is arranged in an electrical or wireless communication with the extracorporeal flow line. Advantageously, the control unit communicates with the first and/or any further injection device and the diagnostic unit, and/or with the separation unit. The control unit preferably is arranged to monitor the treatment assembly. It preferably receives the data providing information about the immunological status of the patient, and controls the first and/or any further injection steps. The control unit preferably comprises a computer with hardware and software components for controlling various parameters. These parameters, which also can influence each other, include at least one of the following: flow rate, injection rate, injection time, concentration of magnetic particles, concentration of binding agent, concentration of target molecules, body fluid temperature, pressure, operating times, operation of the magnetic separation unit, cycle times (number of samples to be treated, or number of cycles in case of continuous flow of blood from the patient's body through the extracorporeal flow circuit and back into the patient's body). The assembly preferably comprises a user interface for monitoring and manipulating the various parameters. Said user interface e.g. can display a therapy status and interact with the injection device. Thus, it is possible to vary the amount of mixture injected, and the concentrations of the functionalized magnetic particles injected, as well as to select the necessary type(s) of binding agent for injection. Preferably, the components of the assembly are in electrical or wireless communication with a processor, preferably located in the control unit.

According to a further preferred embodiment, as mentioned above, the assembly comprises at least a second injection device, by which a second mixture containing functionalized magnetic particles is added to the extracorporeal flow line comprising the body fluid extracted from the patient. The second injection device can be arranged upstream of, downstream of, or together with the first injection device, wherein the first injection device and the second injection device are each individually controlled separate from each other by a control unit, based on data providing information about the immunological status of the patient. It is especially preferable if the functionalized magnetic particles contained in the second mixture are bound to a second binding agent different from the first binding agent and directed against at least a second type of target molecule contained in the body fluid and different from the first target molecule, or in that in the second injection device the functionalized magnetic particles contained in the second mixture are bound to the first binding agent, but are present in a different concentration in the second mixture than in the first mixture. The second injection device can be arranged upstream of, downstream of, or together with the first injection device, wherein the first injection device and the second injection device are each individually controlled separate from each other by a control unit, either by the same or by different control units.

As mentioned above, the injection can be carried out by using an injection-cartridge already containing the first and/or the second and/or further mixture. In this case, the first and/or second and/or further mixture preferably is a pre-mixed suspension of functionalized magnetic nanoparticles already bound to at least a first and/or second and/or further binding agent directed at least against one or more types of target molecules.

Alternatively, the assembly can comprise an injection device having one inlet from a first reservoir of magnetic particles and one inlet from at least a second reservoir containing the at least first binding agent. In this case, the dosing/concentration of the ingredients/constituents is pre-calculated and preferably controlled by a control unit. If the pattern of the immunological response of the respective patient is known, (discharge of immune activators/suppressors), the injection of pre-mixed suspensions of functionalized magnetic nanoparticles can be carried out in a predetermined pattern concerning dose and time of injection. By providing more than one injection device, the treatment can be adjusted over time. The injected mixtures can be varied, e.g. in terms of the type or concentration or injection rate or time. Different possibly necessary mixtures can be prepared ahead of time, e.g. bought over the counter, and stored, ready for use, or pre-connected each to an individual injection device until use.

A preferred embodiment of the assembly comprises, as mentioned above, at least one reservoir associated with the first and/or the second or any further injection device, wherein the at least one reservoir comprises the magnetic particles to be injected by the corresponding injection device. The reservoir may contain a buffer or other suitable reagents. The reservoir may comprise a sensor for detecting the fluid level, temperature or other properties of its contents. The sensors preferably are in electrical or wireless communication with a processor, possibly being part of a control unit. Preferably, the reservoir is disposable, while possibly necessary electronic accessories preferably are reusable. It is of advantage, if the reservoir contains an agitator in case of mechanical dispersion or an ultrasonic probe in case of dispersion by ultrasound.

The body fluid that is transported through the extracorporeal flow line is typically contained within tubing between the different units of the assembly, i.e. the extracorporeal flow line. The tubing can comprise any diameter suitable for the selected flow rate and medical use. Suitable tubing materials include thermoplastics, such as polyvinylchloride, polycarbonate, polyurethane, and urethane, and mixtures or combinations thereof.

According to a further preferred embodiment of the invention, the assembly comprises a fluid pump device for pumping the body fluid through the flow line. In case of a continuous flow line, the flow line is interconnected between the patient's artery and vein, and thus, there is no need for any pump means due to the typically existing pressure difference between the artery and the vein. A further preferred embodiment of the assembly further contains an incubation unit for allowing the target molecules to bind to the binding agents, preferably upstream of a separate mixing unit. As an alternative, a mixing element is included in the incubation unit and can be driven by a control unit.

Further preferred embodiments of the assembly further comprise at least one of the following: a conditioning unit, a thrombus filter unit, a valve, a heat exchanger, a drip chamber, a pressure sensor, a flow sensor, a dispersion sensor, a temperature sensor, a complexation sensor.

In case the assembly comprises at least one conditioning unit for conditioning the magnetic particles for injection by the corresponding injection device, the conditioning preferably is a dispersion unit, in which the nanoparticles are dispersed so as to be optimally distributed for injection. In case the assembly comprises a dispersion unit, it is preferably located upstream of the injection device, i.e. preferably the magnetic particles to be injected are dispersed prior to being injected.

The conditioning preferably is carried out based on the data obtained from the patient's body fluid providing information about the immunological status of the patient and controlled by the control unit, or according to pre-determined standards.

Optionally, the assembly comprises at least one pressure sensor for sensing the fluid pressure of the body fluid within the flow line. Additionally, it can be advantageous to provide one or more valves which facilitate and regulate the flow of body fluid through the extracorporeal flow line, especially at the outlet from the flow line which is to be attached on the patient's body for returning the treated body fluid back to the patient, or at an inlet to be attached on the patient's body for injecting the treated body fluid sample back to the patient, respectively.

One preferred embodiment of the present invention comprises at least one sensor for determining the level of complexation between the magnetic particles and a selected type of target molecule. If the level of complexation is sufficient, the processor/control unit, which receives data from the sensor, will direct the body fluid onward towards the separation unit. If the level of complexation is insufficient, the processor will guide the body fluid back to the injection device or direct a downstream injection device to inject an additional dose of calculated concentration of the selected functionalized magnetic particles bound to the first and/or second binding agent into the body fluid for optimization.

The present invention further concerns the use of the above described assembly for carrying out a method described above for magnetic separation-based body fluid purification of a body fluid of a patient suffering from a dysregulated immune response, e.g. from sepsis.

The present invention further concerns an injection device for use in the described ex vivo method for extracorporeal treatment of a body fluid of a patient suffering from a dysregulated immune response, e.g. sepsis, or for use in the assembly described above, characterized in that the injection unit comprises at least two injection devices, of which a first injection device comprises magnetic particles bound to at least a first binding agent directed at least against a first type of target molecules in the body fluid, and at least a second injection device comprising magnetic particles bound to at least a second binding agent, different from the first binding agent, said second binding agent being directed at least against a second type of target molecules in the body fluid. Preferably, the first injection device and the at least second injection device are individually controlled separately from each other.

By using the assembly as described above, a method for performing a therapeutic procedure on a patient suffering from a dysregulated immune response, e.g. from sepsis, can be carried out, comprising passing circulating blood from a blood vessel of the patient, through an extracorporeal circuit, and back to a blood vessel of the patient, further comprising a diagnostic step, in which an immunological status of the patient is determined by measuring the concentration of at least a first type of target molecule, i.e. marker, in the blood of the patient.

It is a goal of this novel therapeutic intervention, among others, to restore monocytic responsiveness and improve organ function in patients with sepsis-induced immunosuppression. In contrast to therapeutic strategies of the past, the method according to the present invention focuses on the specific reduction of pathogenic compounds such as LPS or lipotechoic acid, and inflammatory mediators such as cytokines and complement factors. The present invention shall enable physicians to interpret the results of diagnostic tests and rationalize treatment modalities in the most appropriate way.

The inventive treatment especially aims to interrupt the sepsis cascade at several intervention points following a selective, multi-target approach, choosing targets among pathogen associated molecules such as endotoxins and key inflammatory mediators. Due to the unique technology, individual cytokines or other inflammatory mediators can be targeted without affecting others. This allows to distinguish between pro- and anti-inflammatory molecules and to apply magnetic blood purification to restore immune balance in patients with a dysregulated immune response, e.g. septic shock patients. The present invention provides a treatment method which can be adapted to the individual immune status of the patient and can be adapted over the course of the treatment diagnosis, according to the patient's need. The inventive technology allows a more selective, efficient, and milder removal of disease related compounds from patients' blood compared to traditional blood filtering methods, dialysis and hemoperfusion.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 shows three possible different treatment methods; wherein

DESCRIPTION OF PREFERRED EMBODIMENTS

Figure 1A:
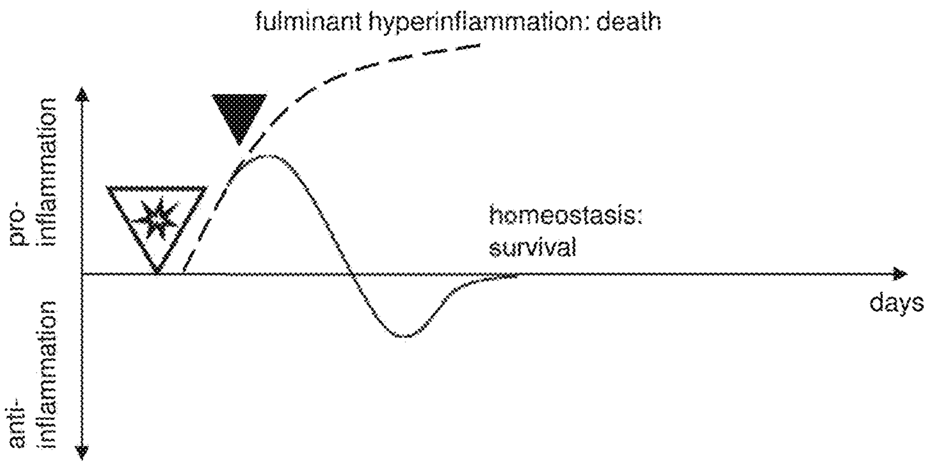
FIG. 1A shows a fight against hyper-inflammation by removing hyper-inflammatory mediators.
Figure 1B:
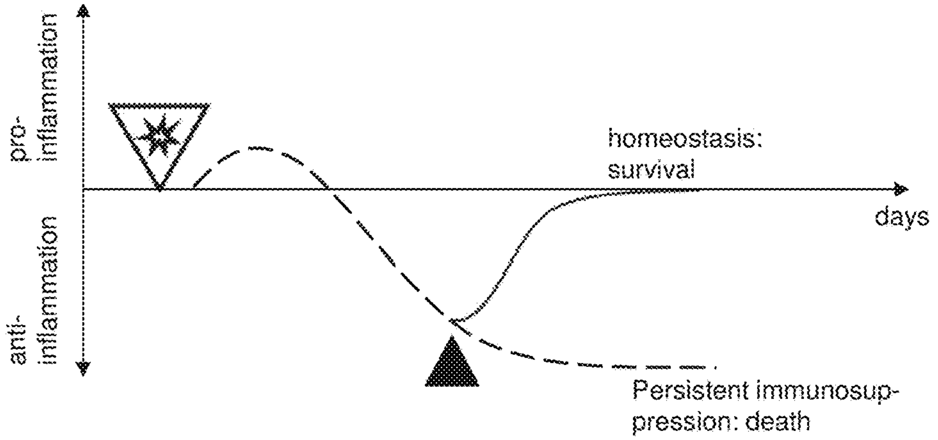
FIG. 1B shows a restoration of immune competence by removing immunosuppressant mediators.
Figure 1C:
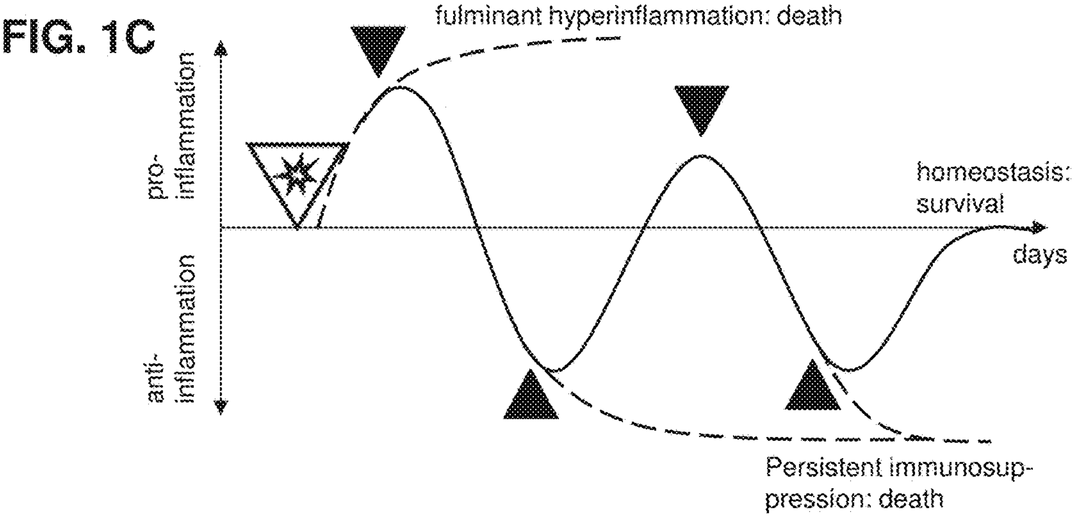
FIG. 1C shows a balancing of hyper-inflammation and immunosuppression.
Figure 1C:
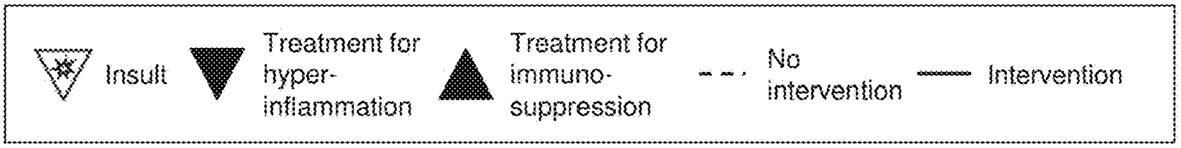

In FIGS. 1A-1C, the immune response of three exemplary patients to an "injury", i.e. pathogenic insult is shown, including the influence of the extracorporeal treatment in each case. As described above, each patient has an individual immune status, depending, among others, on his clinical symptoms, age, comorbidities, or time point of treatment.

Example A: Removal of Hyperinflammatory Mediators

In case of sepsis, the response according to a first model A rapidly sets in with both proinflammatory and anti-inflammatory reactions. Severe sepsis is characterized by an overwhelming hyperinflammatory phase, including fever and abnormally increased circulatory volume, resulting in septic shock. Cardiovascular collapse, metabolic derangements, and multiple organ dysfunction are the main causes of death in such severe cases of septic shock. Treatments include short acting therapies with anti-inflammatory or anticytokine agents.

In patient A, as shown in FIG. 1A, following a pathogenic insult, hyperinflammation is suspected after standard examination and following "surviving sepsis campaign". The primary infection is identified as a gram-negative infection. Based on this diagnosis, LPS and pro-inflammatory cytokines (the early pro-inflammatory cytokines IL-1, TNFα, and IL-18) are removed from the blood in the extracorporeal treatment according to the invention. For this purpose, injecting functionalized magnetic particles bound to a first binding agent directed against LPS, e.g. selected from polymyxin B or a derivative thereof, a monoclonal antibody directed against LPS, mannose-binding lectin, or polyethyleneimine (PEI), is added to the extracorporeal flow line comprising blood extracted from patient A. Then, a second injection of functionalized magnetic particles bound to a second binding agent against IL-1, e.g. a monoclonal antibody, is carried out, followed by a third injection of functionalized magnetic particles bound to a third binding agent against TNFα, e.g. a monoclonal antibody, and a fourth injection of functionalized particles bound to a fourth binding agent against IL-18, e.g. a monoclonal antibody. Alternatively, one or more pre-mixed injection mixtures, e.g. a special, "hyperinflammatory mix", containing multiple functionalized magnetic particles with the multiple necessary binding agents directed against various target molecules is used. The treated blood is returned into the circulatory system of patient A. After 6 hours, measurement of the concentration of TNFα and IL-1 show a decreased level of these targets with a short circulation time. Therefore, the dosing of TNF alpha and IL-1 sorbents (binding agents) are reduced.

After 8 hours, the pathogen strain is identified and the most potent appropriate antibiotic is administered. An antibiotic-induced LPS-release is foreseen, which is why the dosing of LPS-removal (sorbents/binding agents against LPS) is increased. As LPS has various sources, the efficiency of LPS removal can be increased by applying a mixture of different binding agents directed against LPS, e.g. consisting of a monoclonal antibody against LPS and polymyxin B or a derivative thereof.

After the hyperinflammatory phase, patient A goes through a short counterbalancing phase of immunosuppression and recovers.

Therefore, if a hyper-inflammation is detected, hyperinflammatory mediators are removed.

Example B: Removal of Immunosuppressant Mediators

Comorbidities, especially in elderly patients, can impair the immune response. In patients responding according to this second model B, the development of sepsis can result in a blunted or absent hyperinflammatory phase, and a rapid development of an anti-inflammatory state. In this case, immunoadjuvant therapy serves as the treatment of choice. In patient B, the primary infection is identified as a gram-positive infection. Following the pathogenic insult, it is possible that patient B reacts with a normal inflammatory phase, followed by a phase of immunosuppression (as shown). However, it is also possible, that, analogous to patient A, the patient first displays a phase of hyperinflammation (not shown in Figure B). Based on the diagnosis of a gram-positive infection, in case a hyperinflammation is suspected after standard examination and following "Surviving Sepsis Campaign", lipotechoic acid and pro-inflammatory cytokines (the early pro-inflammatory cytokines IL-1, TNFα, and IL-18) are removed from the blood in the extracorporeal treatment according to the invention. For this purpose, injecting functionalized magnetic particles bound to a first binding agent directed against lipotechoic acid, e.g. a monoclonal antibody, is added to the extracorporeal flow line comprising blood extracted from patient B. Then, a second injection of functionalized magnetic particles bound to a second binding agent against IL-1, e.g. a monoclonal antibody, is carried out, followed by a third injection of functionalized magnetic particles bound to a third binding agent against TNFα, e.g. a monoclonal antibody, and a fourth injection of functionalized particles bound to a fourth binding agent against IL-18, e.g. a monoclonal antibody. Alternatively, one or more pre-mixed injection mixtures, containing multiple functionalized magnetic particles with the multiple necessary binding agents directed against various target molecules is used, e.g. a special, "immunosuppression mix".

The treated blood is returned into the circulatory system of patient B. After 6 hours, measurement of the concentration of TNFα and IL-1 show a decreased level of these targets with a short circulation time. Therefore, the dosing of TNF alpha and IL-1 sorbents (binding agents) is reduced.

After 2 days of a possible hyper-inflammatory phase (analogous to patient A) or a normal inflammatory phase (contrary to patient A), as shown in FIG. 1B, patient B falls into a persistent immunosuppression as confirmed by mHLA-DR measurement, which increases the risk of secondary infections and of death. Despite the insult being from a gram-positive pathogen, high levels of LPS are measured due to translocation from the gut, as the membrane of the gut often becomes damaged and thus, permeable. Therefore, a removal of LPS is initiated. Furthermore, the removal of IL-10, IL-6 and C5a is initiated, as their overexpression (high concentrations) leads to an impaired immune response. The removal of IL-10, IL-6, C5a, and LPS lead to a restored immune function as confirmed by mHLA-DR. Patient B survives.

Therefore, if immune competence is impaired, immune competence is restored by removing immunosuppressant mediators.

Example C: Restoration of Balance of Immune Response

A third model C of a possible immunological response to sepsis shows a cycling between hyperinflammatory and hypoinflammatory or immunosuppressive states. If such patients develop sepsis, they display an initial hyperinflammatory response, followed by a hypoinflammtory state/or phase of immunosuppression. In case of a secondary infection, such patients can develop a repeated hyperinflammatory response, leading either to recovery or to a re-entry of the hypoinflammatory phase, with the danger of a severe immunosuppression.

In Patient C, as shown in FIG. 1C, hyper-inflammation is detected after standard examination and following "Surviving Sepsis Campaign". The primary infection is identified as a gram-negative infection. Based on this diagnosis, LPS and pro-inflammatory cytokines (the early pro-inflammatory cytokines IL-1, TNFα, and IL-18, which have a short circulation time) are removed from the blood in the extracorporeal treatment according to the invention. For this purpose, injecting functionalized magnetic particles bound to a first binding agent directed against LPS, e.g. selected from polymyxin B or a derivative thereof, a monoclonal antibody directed against LPS, mannose-binding lectin, or polyethyleneimine (PEI) (as in patient A), is added to the extracorporeal flow line comprising blood extracted from patient C. Then, a second injection of functionalized magnetic particles bound to a second binding agent against IL-1, e.g. a monoclonal antibody, is carried out, followed by a third injection of functionalized magnetic particles bound to a third binding agent against TNFα, e.g. a monoclonal antibody, and a fourth injection of functionalized particles bound to a fourth binding agent against IL-18, e.g. a monoclonal antibody. Here too, it is possible, to use premixed injection mixtures, e.g. "hyper-/hypo-mixtures" containing multiple functionalized magnetic particles with the multiple necessary binding agents directed against various target molecules.

The treated blood is then returned into the circulatory system of patient C. After 2 days of hyper-inflammatory phase, patient C falls into a persistent immunosuppression as confirmed by mHLA-DR measurement, which increases the risk of secondary infection and death. High levels of LPS are measured due to translocation from the gut. Therefore, a removal of LPS is initiated. Furthermore, the removal of IL-10, IL-6, TGFβ and C5a is initiated from day 3-5, as their overexpression (high concentrations) leads to an impaired immune response.

A hyper-inflammatory phase is treated on day 6 with the removal of pro-inflammatory cytokines (see above). Immunosuppression is then treated on day 7-8, leading to recovery of patient C.

Therefore, if an imbalance of hyper-inflammation and immunosuppression is detected, the balance is restored by treatment of each phase separately and subsequently.

Figure 2:
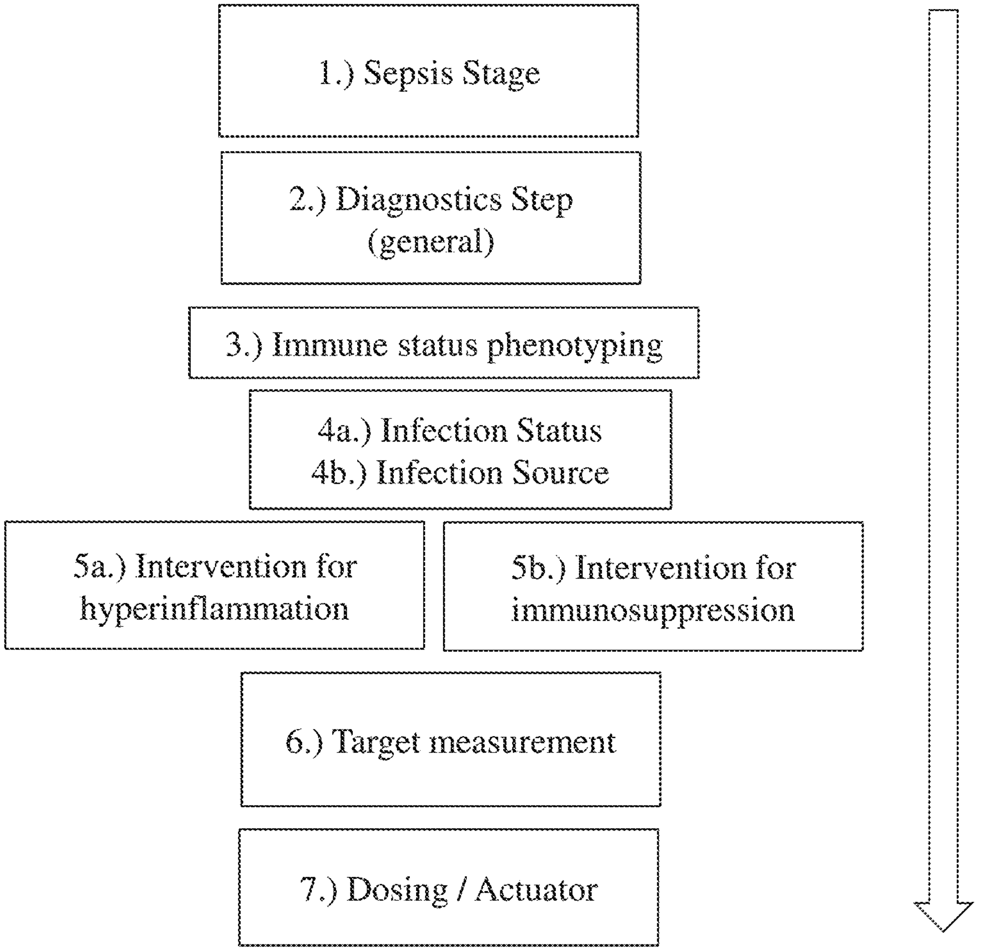
FIG. 2 shows a flow chart of the various diagnostic and phenotyping steps based on which the extracorporeal treatment is based.

FIG. 2 shows a flow chart of the steps leading to the control of the extracorporeal treatment according to the invention:

Based on clinical symptoms, the emergency physician or intensive care physician suspects either a hyper-inflammation or an immunosuppression (or persistent, inflammation, immunosuppression and catabolic syndrome (PICS)). Based on this suspicion, the immune status or function is first evaluated by checking general clinical criteria, i.e. general markers, such as body temperature, heart rate, respiratory rate, and general organ function.

General Criteria for SIRS are the Following:

- body temperature: Temp >38° C. (100.4° F.) or <36° C. (96.8° F.)
- heart rate: >90
- respiratory rate: >20 or $PaCO_2$<32 mm Hg ($PaCO_2$—arterial carbon dioxide tension)
- leukocyte count (WBC): >12,000/mm$^3$, <4,000/mm$^3$, or >10% bands When a patient presents with two or more SIRS criteria but with hemodynamic stability (i.e. blood pressure at baseline), a more detailed clinical assessment must be made to determine the possibility of an infectious etiology.

Furthermore, the procalcitonin (PCT) test is used by emergency and intensive care physicians for the diagnosis of sepsis. Procalcitonin is a considered the most significant biomarker for severe inflammations and infections. Normally, PCT only occurs in the blood in very low concentrations. Its production and release can be stimulated by almost every organ by inflammatory cytokines and bacterial endotoxins. Therefore, the higher the concentration of PCT, the more likely is a systemic infection and a sepsis.

If an infection is suspected or confirmed based on standard monitoring, the patient is diagnosed with sepsis and a lactate level is obtained to determine the degree of hypoperfusion and inflammation. Severe sepsis is diagnosed in case of organ dysfunction, hypotension or hypoperfusion, for which a lactic acidosis can be an indicator, if the systolic blood pressure is <90 or drops >40 mm Hg of normal. A lactate level ≥4 mmol/L is considered an indicator for Severe Sepsis, and aggressive management with broad spectrum antibiotics, intravenous fluids, and vasopressors should be initiated (aka EGDT). Severe sepsis with hypotension, despite adequate fluid resuscitation, is an indicator for septic shock. Patients that present with a suspected or confirmed infection and hemodynamic instability should immediately be treated for septic shock. While SIRS criteria will likely be present in these patients, aggressive management should not be delayed while waiting for laboratory values such as the WBC or lactate. In case of evidence of two or more organs failing, multiple organ dysfunction syndrome is diagnosed. Early recognition of sepsis, severe sepsis, and septic shock, and early administration of broad spectrum and organism specific antibiotic are the most critical actions.

In case the patient is in a phase of hyper-inflammation, the infection source is then identified as being either bacterial, viral or fungal. In case of bacterial infections, the infection source can further be specified as the bacteria being gram-negative or gram-positive. After the active infection source has been identified, the treatment is selected, depending on the infection source.

If the patient is found to be in a state of immunosuppression, especially if the patient is found to belong to a high-risk subgroup, an immune status phenotyping is carried out.

After a sepsis has been clinically diagnosed, treatment following the "Surviving Sepsis Campaign" is immediately induced. Meanwhile, the phenotype of the immune status is further specified by phenotyping, i.e. by assaying the concentration of various target substances/markers. The measurement of target substances/markers is carried out preferably by an endotoxin activity assay (EAA test) in case of lipopolysaccharides, and by an enzyme-linked immunosorbent assay (ELISA) in case of cytokines/complement factors. Further characterizing of the immune status and a more precise etiology is possible by assaying the genomics and metabolomics of the patient.

The proposed treatment, which can be adapted based on the results of phenotyping, comprises an adaptive treatment for inflammation patients, wherein the therapeutic assembly includes one or several defined sorbents, preferably magnetic nanosorbents, equipped with specific affinity binders, e.g. antibodies towards inflammation targets, e.g. for LPS, TNF, IL6, IL8, IL10, and preferably also C3a, C5a. One or several of these sorbents are dosed according to the immunological status of the patient, i.e. based on the results of the above described diagnostic step, preferably including immune status phenotyping. Over the duration of treatment, the injection mixture(s), i.e. the sorbent-/binding agent mixtures can be adapted to the actual immune status of the patient over time. Repeated diagnostic tests of the body fluid before and after one or more cycles of treatment, allow the adjustment of the type and/or concentration and/or amount of injected functionalized magnetic nanosorbents.

Proposed Treatment Options:

Target molecules to be removed in case of hyper-inflammation as a result of gram-negative bacterial infection:

Primary infection pathogen, i.e. whole bacteria

Primary infection PAMPS (pathogen-associated molecular patterns): LPS, bacterial toxins, flagellin, bacterial RNA/DNA, peptidoglycan Pro-inflammatory immune mediators: TNFα, IL-1, IL-6, IL-8, IL-15, IL-18, GM-CSF, IFNγ

Complement factors: C5a, C3a

Target molecules to be removed in case of hyper-inflammation as a result of gram-positive bacterial infection:

Primary infection pathogen, i.e. whole bacteria

Primary infection PAMPS: lipotechoic acid, bacterial toxins, flagellin, bacterial RNA/DNA, peptidoglycan Pro-inflammatory immune mediators: TNFα, IL-1, IL-6, IL-8, IL-15, IL-18, GM-CSF, IFNγ

Complement factors: C5a, C3a

Target molecules to be removed in case of hyper-inflammation as a result of gram indefinite bacterial infection:

Primary infection pathogen, i.e. whole bacteria

Primary infection PAMPS: bacterial toxins, flagellin, bacterial RNA/DNA, peptidoglycan Pro-inflammatory immune mediators: TNFα, IL-1, IL-6, IL-8, IL-15, IL-18, GM-CSF, IFNγ

Complement factors: C5a, C3a

Target molecules to be removed in case of hyper-inflammation as a result of viral infection:

Virus

Primary infection PAMPS: viral RNA/DNA, peptidoglycan

Pro-inflammatory immune mediators: TNFα, IL-1, IL-6, IL-8, IL-15, IL-18, GM-CSF, IFNγ

Complement factors: C5a, C3a

Target molecules to be removed in case of hyper-inflammation as a result of fungal infection:

Fungal cells

Primary infection PAMPS: fungal toxins, chitin, fungal DNA/RNA

Pro-inflammatory immune mediators: TNFα, IL-1, IL-6, IL-8, IL-15, IL-18, GM-CSF, IFNγ

Complement factors: C5a, C3a

Target molecules to be removed in case of hyper-inflammation, despite an already resolved primary infection, when the main problem is a secondary infection or an imbalance of the immune system:

Primary infection PAMPS: LPS (e.g. entered the vascular system through a perforated membrane of the intestines);

DAMPS (damage-associated molecular patterns): HMGB1, histone, cell DNA/RNA

Pro-inflammatory immune mediators: TNFα, IL-1, IL-6, IL-8, IL-15, IL-18, GM-CSF, IFNγ

Complement factors: C5a, C3a

Target molecules to be removed in case of immunosuppression with a still active infection source:

Primary infection PAMPS: according to infection type, see above;

DAMPS: HMGB1, histone, cell DNA/RNA

Cytokines with immunosuppressive effect: IL-6, IL-10, IL-33, TGFβ

Complement factors: C5a, C3a

Target molecules to be removed in case of immunosuppression despite a resolved primary infection, when the main problem is a secondary infection or an imbalance of the immune system:

Primary infection PAMPS: LPS (e.g. entered the vascular system through a perforated membrane of the intestines);

DAMPS: HMGB1, histone, cell DNA/RNA

Cytokines with immunosuppressive effect: IL-6, IL-10, IL-33, TGFβ

Complement factors: C5a, C3a

The treatment steps shown in FIG. 2 do not have to be applied in a linear fashion, as the treatment steps can also be part of a feedback loop, wherein one or more steps is/are controlled based on the diagnostic data collected at different points in time and thus based on a possible algorithm implemented in a computer program or translated into instructions for medical personnel.

Figure 3:
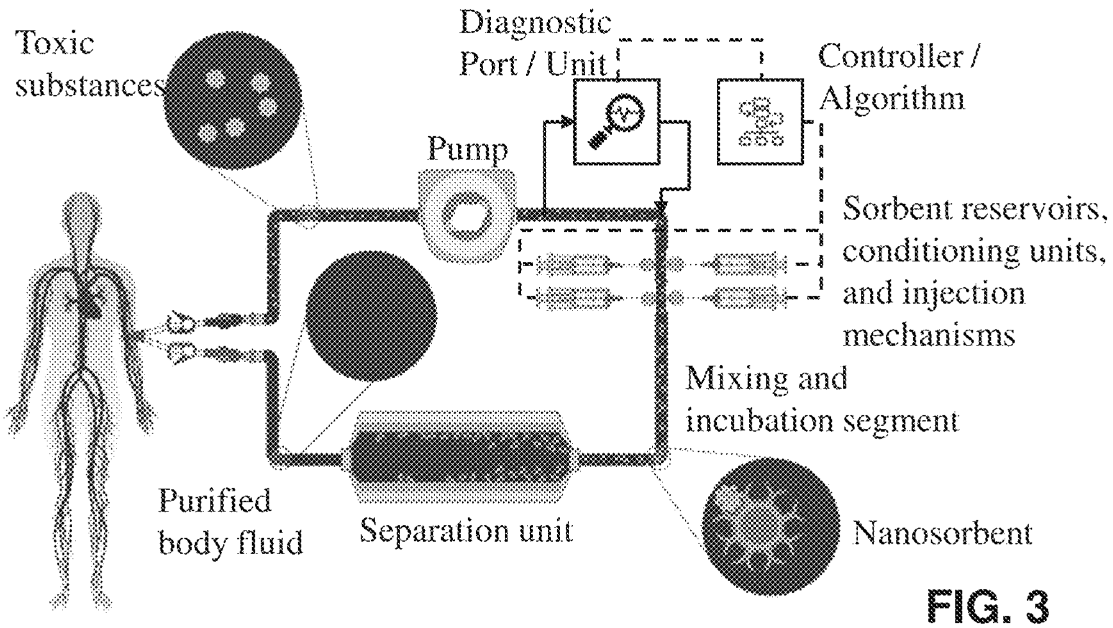
FIG. 3 shows a simplified schematic representation of the assembly of extracorporeal treatment method.

A schematic overview of the assembly according to the present invention is shown in FIG. 3. In this specific embodiment, the assembly comprises an extracorporeal circuit, i.e. an extracorporeal flow line. This extracorporeal flow line can be connected to a body of a patient suffering from a dysregulated immune response, for continuous treatment or purification of the body fluid, which in this case is blood. However, the extracorporeal circuit can be disconnected from the patient's body and samples of the untreated blood previously extracted from the patient's body can be injected into an inlet port of the extracorporeal flow line. The untreated blood is diagnosed in a diagnostic unit connected to or associated with the extracorporeal flow line. In the embodiment shown in FIG. 3, the diagnostic results are interpreted by a controller that actuates the injection devices and doses the suitable nanosorbents. The blood is driven through the extracorporeal flow line by a blood pump. The depicted assembly further can contain at least one sorbent reservoir and/or at least one conditioning unit (not shown). Four injection units/devices are shown in form of injection ports into which separate pre-mixed injections mixtures, containing functionalized nanomagnets are attached for injection of the respective injection mixtures into the untreated blood flowing in the extracorporeal flow line. Following the injection step, the blood is mixed and incubated for sufficient complexation of the target molecules to the binding agents, i.e. nanosorbents. In the embodiment shown, the mixing- and incubation steps are carried out in a segment of the extracorporeal flow line. After a sufficient, possibly pre-defined level of complexation is reached, the blood is directed through a separation unit, in which the magnetic particles are separated from their binding agents, which now are bound to toxic substances or target molecules, the removal, i.e. total removal or reduction of concentration, of which is the result of the treatment. The end product of such a single "cycle" or pass of the extracorporeal treatment is purified blood, which can either be continuously directed back into the patient's body or extracted at the outlet port of the extracorporeal flow line for storage, further treatment cycles (possibly with other binding agents) or return to the body of the patient at a later point in time.

The invention claimed is:

1. A method for extracorporeal treatment of a body fluid of a patient suffering from a dysregulated immune response, in an extracorporeal flow line, comprising removing at least one harmful substance from the body fluid of the patient, comprising the following steps:

at least a first injection step, in which, by means of a first injection device, a first mixture containing functionalized magnetic particles bound to at least a first binding agent at least directed against a first type of target molecules contained in the body fluid is added to the extracorporeal flow line comprising a sample of the body fluid extracted from the patient suffering from the dysregulated immune response, e.g. sepsis, and containing at least the first type of target molecules, in a therapeutically effective dose necessary to reduce a concentration of the target molecules of at least the first type in the sample of body fluid of the patient, subsequently, mixing the body fluid comprising the functionalized magnetic particles to ensure sufficient binding of the target molecules of at least the first type to the functionalized magnetic particles; and separating the functionalized magnetic particles bound to the target molecules of at least the first type from the sample of body fluid, such that a concentration of target molecules of at least the first type in the sample of body fluid is reduced, wherein the method further comprises at least a second injection step, in which, by means of a second injection device, a second mixture different from the first mixture and containing functionalized magnetic particles, is added to the extracorporeal flow line comprising the body fluid extracted from the patient, wherein the second injection step is carried out downstream of or simultaneously with the first injection step, wherein in the second injection device, the functionalized magnetic particles contained in the second mixture are bound to a second binding agent different from the first binding agent and directed against a second type of target molecule contained in the body fluid and different from the first target molecule, or wherein in the second injection device the functionalized magnetic particles contained in the second mixture are bound to the first binding agent but are present in a different concentration in the second mixture than in the first mixture;

and wherein the method further comprises, upstream of the first injection step, a diagnostic step, in which data providing information about an immunological status of the patient is obtained by measuring an expression of at least one marker molecule or a concentration of at least one marker molecule in the body fluid of the patient in an assay or by a sensor, and wherein the data obtained in the diagnostic step from the patient's body fluid providing information about the immunological status of the patient is transmitted to a control unit which is arranged in an electrical or wireless communication with the extracorporeal circuit, and wherein the control unit individually controls the first injection step and the second injection step based on the data providing information about the immunological status of the patient and in terms of at least one of the following: type of binding agent, injection rate, time of injection, injection dose, injection concentration, and/or injection pressure, wherein the injection of the second mixture by the second injection device is controlled separately, but in coordination with the injection of the first mixture by the first injection device.

2. The method according to claim 1, wherein the body fluid is blood.

3. The method according to claim 1, wherein the functionalized magnetic particles injected are nano-size magnetic adsorbents.

4. The method according to claim 1, wherein the functionalized magnetic particles each comprise a magnetic core and at least one functional layer.

5. The method according to claim 1, wherein the separation step is carried out by a magnetic filter.

6. The method according to claim 1, wherein the first binding agent is directed at least against a first type of target molecule selected from a group consisting of: pathogen-associated-pattern immune activators, pro-inflammatory mediators, anti-inflammatory mediators, complement factors, and cleavage products thereof.

7. The method according to claim 6, wherein the first binding agent is directed at least against a first type of target molecule selected from a group consisting of: cytokines, nitric oxide, thromboxanes, leukotrienes, phospholipids, prostaglandins, kinins, complement factors, coagulation factors, superantigens, monokines, chemokines, interferons, free radicals, proteases, arachidonic acid metabolites, prostacyclins, beta endorphins, myocardial depressant factors, anandamide, 2-arachidonoylglycerol, tetrahydrobiopterin, cell fragments and chemicals including histamine, bradykinin, and serotonin.

8. The method according to claim 6, wherein the at least first binding agent is directed at least against a first type of target molecule selected from a group consisting of: LPS, lipotechoic acid, TNFα, TGFβ, IL-1, IL-6, IL-8, IL-10, IL-15, IL-18, IL-33, GM-CSF, IFNγ, HMGB1, C5a, C3a, and adrenomedullin.

9. The method according to claim 1, wherein the second binding agent is directed at least against a second type of target molecule selected from a group consisting of pathogen-associated-pattern immune activators, pro-inflammatory mediators, anti-inflammatory mediators, complement factors and cleavage products thereof.

10. The method according to claim 9, wherein the second binding agent is directed at least against a second type of target molecule selected from a group consisting of: cytokines, nitric oxide, thromboxanes, leukotrienes, phospholipids, prostaglandins, kinins, complement factors, coagulation factors, superantigens, monokines, chemokines, interferons, free radicals, proteases, arachidonic acid metabolites, prostacyclins, beta endorphins, myocardial depressant factors, anandamide, 2-arachidonoylglycerol, tetrahydrobiopterin, cell fragments and chemicals including histamine, bradykinin, and serotonin.

11. The method according to claim 9, wherein the second binding agent is directed at least against a second type of target molecule selected from a group consisting of: LPS, lipotechoic acid, TNFα, TGFβ, IL-1, IL-6, IL-8, IL-10, IL-15, IL-18, IL-33, GM-CSF, IFNγ, HMGB1, C5a, C3a, and adrenomedullin.

12. The method according to claim 1, wherein in the first injection step and/or in the second injection step, the first binding agent and/or the second binding agent is selected from a group consisting of: antibodies, peptides, lectines, chemical chelating agents, and polymers.

13. The method according to claim 12, wherein the at least first binding agent and/or the at least second binding agent is an antibody or an aptamer, at least directed against the first type of target molecule and/or the second type of target molecule.

14. The method according to claim 12, wherein the at least first binding agent and/or the at least second binding agent is a monoclonal antibody.

15. The method according to claim 1, wherein in case the patient to be treated suffers from hyper-inflammation as a result of bacterial infection, the at least first binding agent and/or at least the second binding agent is directed at least against a first and/or second type of target molecule selected from a group consisting of: LPS, lipotechoic acid, bacterial toxins, flagellin, bacterial RNA/DNA, peptidoglycan, TNFα, IL-1, IL-6, IL-8, IL-15, IL-18, GM-CSF, IFNγ, and complement factors; and/or wherein in case the patient to be treated suffers from hyperinflammation as a result of viral infection, the at least first binding agent and/or at least the second binding agent is directed at least against a first and/or second type of target molecule selected from a group consisting of: viral RNA/DNA, peptidoglycan, TNFα, IL-1, IL-6, IL-8, IL-15, IL-18, GM-CSF, IFNγ, and complement factors; and/or wherein in case the patient to be treated suffers from hyperinflammation as a result of fungal infection, the at least first binding agent is directed at least against a first and/or second type of target molecule selected from a group consisting of: fungal toxins, chitin, fungal DNA/RNA, TNFα, IL-1, IL-6, IL-8, IL-15, IL-18, GM-CSF, IFNγ, and complement factors; and/or wherein in case the patient to be treated suffers from immunosuppression, the at least first binding agent and/or at least the second binding agent is directed at least against a first and/or second type of target molecule selected from a group consisting of: LPS, lipotechoic acid, bacterial toxins, flagellin, bacterial RNA/DNA, viral RNA/DNA, fungal toxins, chitin, fungal DNA/RNA peptidoglycan, HMGB1, histone, IL-6, IL-10, IL-33, TGFβ, and C5a.

16. The method according to claim 1, wherein an expression of at least one marker molecule or a concentration of at least one marker molecule in the body fluid of the patient is measured in an endotoxin activity assay (EAA) or an enzyme-linked immunosorbent assay (ELISA).

17. An assembly for extracorporeal magnetic separation-based body fluid purification of a patient suffering from a dysregulated immune response, comprising:

an extracorporeal flow line interconnected between an inlet port and an outlet port;

at least a first injection device for injecting, in a first injection step, a first mixture comprising functionalized magnetic particles bound to at least a first binding agent at least directed against a first type of target molecule contained in the body fluid into the extracorporeal flow line;

a mixing unit, for mixing the functionalized magnetic particles in the body fluid after injection of the functionalized magnetic particles to allow a therapeutically effective level of complexation between the functionalized magnetic particles and the first type of target molecule, wherein the mixing unit is arranged downstream of the first injection device along the extracorporeal flow line; and a separation unit comprising a magnetic field region for magnetically separating the functionalized magnetic particles and the target molecules bound thereto from the body fluid, wherein the separation unit is a magnetic filter, and wherein the separation unit is arranged downstream of the mixing unit along the extracorporeal flow line;

wherein the first injection device is controlled based on data obtained from the patient's body fluid providing information about the immunological status of the patient, and wherein the first injection step is controlled in terms of at least one of a group consisting of: injection rate, time of injection, injection dose, injection concentration, and injection pressure, and wherein the assembly further comprises at least a second injection device, by which a second mixture, different from the first mixture, and containing functionalized magnetic particles, is added to the extracorporeal flow line comprising the body fluid extracted from the patient, wherein the second injection device is arranged downstream of or together with the first injection device, and wherein in the second injection device, the functionalized magnetic particles contained in the second mixture are bound to a second binding agent different from the first binding agent and directed against a second type of target molecule contained in the sample of body fluid and different from the first target molecule, or wherein in the second injection device the functionalized magnetic particles contained in the second mixture are bound to the first binding agent but are present in a different concentration in the second mixture than in the first mixture, and that the assembly further comprises, downstream of the inlet port and upstream of the first injection device, a diagnostic sample port for extraction of a test sample of the patient's body fluid after entering the extracorporeal flow line at the inlet port;

and wherein the assembly further comprises a control unit which is arranged in an electrical or wireless communication with the extracorporeal flow line, for the control of the first injection device and the second injection device based on data obtained from an external or associated diagnostic unit about the patient's body fluid extracted via the diagnostic sample port, said data providing information about the immunological status of the patient, wherein the external or associated diagnostic unit is adapted for measuring an expression of at least one marker molecule or a concentration of at least one marker molecule in the body fluid of the patient by means of an assay or by a sensor, wherein the control unit is arranged to individually control the first injection device and the second injection device, and wherein the first injection device and the second injection device are controlled by the control unit in terms of at least one of the following: type of binding agent, injection rate, time of injection, injection dose, injection concentration, injection pressure, wherein the injection of the second mixture by the second injection device is controlled separately, but in coordination with the injection of the first mixture by the first injection device.

18. The assembly according to claim 17, wherein the assembly further comprises at least one of a group consisting of: a pump device for pumping the body fluid flow through the flow line, an incubation unit, a conditioning unit, a thrombus filter unit, a valve, a heat exchanger, a drip chamber, a pressure sensor, a flow sensor, a dispersion sensor, and a temperature sensor.

19. The assembly according to claim 18, wherein the assembly comprises a conditioning unit in the form of a dispersion unit.

20. The assembly according to claim 17, wherein the assembly further comprises at least one reservoir associated with the first injection device, and wherein the reservoir comprises the magnetic particles to be injected by at least the first injection device.

21. The assembly according to claim 20, wherein the reservoir is disposable.

22. The assembly according to claim 17, wherein the functionalized magnetic particles are nano-size magnetic absorbents.

23. The assembly according to claim 17, wherein the separation unit is a permanent magnetic filter.

24. The assembly according to claim 17, wherein the control unit comprises a user interface.

* * * * *